United States Patent
Eichler

(10) Patent No.: US 10,028,861 B2
(45) Date of Patent: Jul. 24, 2018

(54) CONTROL ARRANGEMENT FOR AN OPHTHALMIC SURGICAL SYSTEM

(71) Applicant: Carl Zeiss Meditec AG, Jena (DE)

(72) Inventor: Michael Eichler, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 556 days.

(21) Appl. No.: 14/671,732

(22) Filed: Mar. 27, 2015

(65) Prior Publication Data
US 2015/0202081 A1 Jul. 23, 2015

Related U.S. Application Data

(63) Continuation of application No. PCT/EP2013/002835, filed on Sep. 20, 2013.

(30) Foreign Application Priority Data

Sep. 27, 2012 (DE) .................. 10 2012 018 982

(51) Int. Cl.
*A61B 17/20* (2006.01)
*A61F 9/007* (2006.01)
*A61M 1/00* (2006.01)

(52) U.S. Cl.
CPC ...... *A61F 9/00745* (2013.01); *A61F 9/00736* (2013.01); *A61M 1/0025* (2014.02);
(Continued)

(58) Field of Classification Search
CPC ............ A61F 9/00736; A61F 9/00745; A61M 1/0025; A61M 1/0039; A61M 2205/058;
(Continued)

(56) References Cited

U.S. PATENT DOCUMENTS

| | | | |
|---|---|---|---|
| 8,920,360 B2 | 12/2014 | Kraus et al. | |
| 2002/0013574 A1 | 1/2002 | Elbrecht et al. | |
| 2006/0195076 A1* | 8/2006 | Blumenkranz | A61F 9/00736 606/4 |

FOREIGN PATENT DOCUMENTS

| | | | | |
|---|---|---|---|---|
| DE | 102010047011 A1 * | 4/2012 | ......... | A61F 9/00745 |
| WO | 2007/073802 A1 | 7/2007 | | |

OTHER PUBLICATIONS

International Search Report dated Jan. 20, 2014 of international application PCT/EP2013/002835 on which this application is based.
(Continued)

*Primary Examiner* — Kevin C Sirmons
*Assistant Examiner* — Leah Swanson
(74) *Attorney, Agent, or Firm* — Walter Ottesen, P.A.

(57) ABSTRACT

A control arrangement for an ophthalmic surgical system for phacoemulsifying a lens wherein the system includes an aspiration line for drawing off fluid and shattered lens particles of the eye lens and a phaco handpiece having a needle. The aspiration line runs within the needle and is configured to impart ultrasonic energy to the phaco handpiece for shattering the eye lens via a longitudinal vibration of the needle. The control arrangement includes a transmitter configured to irradiate electromagnetic radiation via the aspiration line and a receiver configured to receive at least a part of the radiation; and, a control unit configured to control an absolute value of a parameter of the ophthalmic surgical system in dependence upon the amount of the received electromagnetic radiation.

8 Claims, 8 Drawing Sheets

(52) U.S. Cl.
CPC ..... *A61M 1/0039* (2013.01); *A61M 2205/058* (2013.01); *A61M 2205/3313* (2013.01); *A61M 2205/3334* (2013.01); *A61M 2205/3344* (2013.01); *A61M 2205/3375* (2013.01); *A61M 2210/0612* (2013.01)

(58) Field of Classification Search
CPC .. A61M 2205/3313; A61M 2205/3334; A61M 2205/3344; A61M 2205/3375; A61M 2210/0612
See application file for complete search history.

(56) References Cited

OTHER PUBLICATIONS

Translation of International Preliminary Report on Patentability and Written Opinion dated Apr. 9, 2015 of international application PCT/EP2013/002835 on which this application is based.

\* cited by examiner

CONTROL ARRANGEMENT FOR AN OPHTHALMIC SURGICAL SYSTEM

CROSS REFERENCE TO RELATED APPLICATIONS

This application is a continuation application of international patent application PCT/EP2013/002835, filed Sep. 20, 2013, designating the United States and claiming priority from German application 10 2012 018 982.6, filed Sep. 27, 2012, and the entire content of both applications is incorporated herein by reference.

FIELD OF THE INVENTION

The invention relates to a control arrangement for an ophthalmic surgical system for phacoemulsification of an eye lens and an ophthalmic surgical system having such a control arrangement.

BACKGROUND OF THE INVENTION

There is a plurality of surgical techniques for treating eye lens clouding, which is denoted in medicine as a cataract. The most widespread technique is phacoemulsification, in which a thin needle is introduced into the eye lens and excited to vibrate by means of ultrasound. In its direct vicinity, the vibrating needle emulsifies the lens in such a way that the resulting lens particles can be suctioned away through a line by means of a pump. A rinsing fluid (irrigation fluid) is supplied in the process, the particles and the fluid being suctioned away through an aspiration line which is usually arranged inside the needle. Once the lens has been completely emulsified and removed, a new, artificial lens can be inserted into the empty capsular bag so that a patient being treated in such a way can regain good visual acuity.

A cataract surgical procedure is an intervention with relatively low complication rate and large patient numbers. However, the relatively low complication rate can be achieved only when a highly experienced surgeon carries out the surgical procedure. When the eye lens is being comminuted by a needle tip vibrating with ultrasound, during the surgery a relatively large particle is unavoidably placed in front of a needle tip such that a needle tip and/or its suction opening is blocked. This state is denoted as occlusion. In such a case, the suction pressure inside the aspiration line rises sharply, emulsification being interrupted at this time. The fluid and the small particles can be suctioned off usually only when, for example owing to a very high input of energy, a sharp increase in suction pressure or to a reversal of the aspiration pump running direction, the particle is once again removed from the needle tip. It follows that a stoppage is broken up at such a time, there being a sudden decrease in the previously applied high vacuum. The suction thus resulting can have the effect that not only small particles and fluid are sucked toward the aspiration needle, but also that a part of the capsular bag comes into contact with the needle. When the capsular bag is penetrated, this leads to substantial complications for the patient which must be avoided unconditionally. When an occlusion is imminent, an experienced operator has developed over time a knack of breaking it up. Nevertheless, a risk always remains that the patient's eye could be damaged.

SUMMARY OF THE INVENTION

It is an object of the invention to provide a control arrangement for an ophthalmic surgical system for phacoemulsification of an eye lens in the case of the occurrence of an occlusion at or in a phacoemulsification needle, and the breaking up of such an occlusion at or in such a needle, which can be detected quickly and reliably, the phacoemulsification being possible with high efficiency, and a risk of injuring the patient being low. It is also an object to provide an ophthalmic surgical system having such a control arrangement.

The control arrangement of the invention is for an ophthalmic surgical system for phacoemulsifying a lens. The system includes: an aspiration line for drawing off fluid and shattered lens particles of the eye lens; a phaco handpiece having a needle; the aspiration line running within the needle and being configured to impart ultrasonic energy to the phaco handpiece for shattering the eye lens via a longitudinal vibration of the needle; and, the control arrangement comprising: a transmitter configured to irradiate electromagnetic radiation; a coupling unit having a distal end and being configured to so conduct at least one part of the irradiated electromagnetic radiation to the distal end that the at least one part of the electromagnetic radiation can be coupled into the aspiration line; the distal end being disposed outside of the aspiration line; a receiver configured to receive at least a part of the electromagnetic radiation; a control unit configured to control an absolute value of a parameter of the ophthalmic surgical system in dependence upon the amount of the received electromagnetic radiation; and, the electromagnetic radiation having a wavelength greater than 750 nanometers and a pulsed infrared radiation having an irradiance of a maximum of 0.1 W/cm$^2$.

The control arrangement for an ophthalmic surgical system for phacoemulsification of an eye lens has:
- a transmitter suitable for emitting electromagnetic radiation,
- a coupling device which can be used to pass at least a portion of the emitted electromagnetic radiation to a distal end of the coupling device such that the at least one portion of the electromagnetic radiation can be coupled into an aspiration line of the ophthalmic surgical system, the distal end of the coupling device being arranged outside the aspiration line,
- a receiver suitable for receiving at least a portion of the electromagnetic radiation,
- and a control unit which can be used to control an absolute value of a parameter of the ophthalmic surgical system as a function of the absolute value of the received radiation.

The control arrangement according to the invention utilizes the circumstance that electromagnetic radiation has a very high wave propagation velocity. In an aqueous medium such as is present in the case of a fluid in an aspiration line or irrigation line, the velocity is approximately 225 000 km/s. When the radiation is coupled into an aspiration line, it is therefore possible to find out very quickly whether there is an occlusion in the aspiration line and whether the occlusion is just breaking up. Depending on the absolute value of the received radiation, it is then possible to control an associated ophthalmic surgical system appropriately in order to keep down a risk to the patient's eye.

Conventional ophthalmic surgical systems have previously used the pressure profile in an aspiration line to detect an occlusion or the breakthrough of an occlusion. However, a pressure wave propagates only at the speed of sound, that is, at approximately 1.5 km/s. Since flexible hoses are frequently used for an aspiration line, it follows that approximately 3 milliseconds are required to pass the pressure signal along a length of approximately two meters as far as the pressure sensor. According to the Nyquist-Shannon sampling theorem, the determination of a pressure gradient requires at least a further 3 milliseconds. Owing to the control arrangement according to the invention, the detection of the breakthrough of an occlusion, or an occlusion, can be reduced to less than 0.1 ms. It is thereby possible to initiate much more quickly a control of an absolute value of a parameter of the ophthalmic surgical system.

Owing to the very quick wave propagation of the electromagnetic radiation, it is possible to arrange the transmitter very far from a needle of a phacoemulsification handpiece. Since it is possible according to the invention for the electromagnetic radiation to be coupled into an aspiration line by means of a coupling device, the distal end of the coupling device being arranged outside the aspiration line, the fluid can flow without hindrance inside the aspiration line.

Coupling the electromagnetic radiation into the aspiration line can preferably be done directly in the handpiece. It is thereby possible to limit the radiation to the region of the needle and the immediately adjacent aspiration line. The line cross section is smallest in the region, and thus the probability of an occlusion is highest.

In accordance with a preferred embodiment, the receiver can receive the electromagnetic radiation exiting from the aspiration line. When, therefore, no lens particle blocks the aspiration line at the distal end of the aspiration line, an electromagnetic radiation emitted by the transmitter exits from the aspiration line such that the receiver can still receive a relatively great deal of electromagnetic radiation. In the event of an occlusion inside the aspiration line or at the needle tip, no further electromagnetic radiation exits from the distal end of the aspiration line, and so a receiver cannot detect any radiation. If, owing to an increased suction pressure or to increasing longitudinal vibration of the needle of the phaco handpiece, the lens particle is then shattered into small fragments, it is possible for there again to exit at the distal end of the aspiration line electromagnetic radiation which can be detected by the receiver. This difference in the signal strength of the receivable electromagnetic radiation is an indicator that the breakthrough of an occlusion has taken place.

In accordance with a further embodiment of the invention, the receiver can receive the electromagnetic radiation reflected by a lens particle. If a lens particle completely blocks a distal end of an aspiration line, that is, the needle tip, virtually no further electromagnetic radiation can exit from the distal end of the aspiration line. All electromagnetic radiation emitted by a transmitter and coupled into the aspiration line is then reflected by the lens particle blocking the aspiration line. The receiver of the control arrangement according to the invention must then be arranged such that it receives the radiation reflected by the lens particle. If the lens particle breaks owing to increased suction pressure or to vibration of the needle of the phaco handpiece, only a portion of the emitted electromagnetic radiation can still be reflected by the fraction, and so in the case of breakthrough of an occlusion the receiver can receive less electromagnetic radiation. The absolute value of the reflected electromagnetic radiation is therefore an indicator as to whether an occlusion or the breakthrough of an occlusion has taken place.

The electromagnetic radiation preferably has a wavelength of greater than 750 nanometers. Such a radiation is advantageous, since it has a relatively low energy, which means there is a low risk of the eye being damaged thereby. The electromagnetic radiation is preferably a pulsed infrared radiation with a maximum irradiation intensity of 0.1 watt per $cm^2$. This ensures that the retina is not damaged during an ophthalmic surgical procedure even in the case of the retina being illuminated. Thus, the electromagnetic radiation does not serve to warm or heat up a target object, but, entirely on the contrary, merely as measuring radiation which is still just strong enough to be received by a receiver. The electromagnetic radiation does not shatter any lens or lens particle, nor cause coagulation of a tissue. A pulsed radiation is advantageous, since any radiation of similar wavelength in the surroundings which is not pulsed is not taken into account in this way in the evaluation of the signal.

The aspiration line preferably has a line inner wall which reflects the electromagnetic radiation coupled into the aspiration line. Fluid in the aspiration line can serve as a conductor for the electromagnetic radiation, reflection of the radiation at the line inner wall having the effect that a relatively large absolute value of the electromagnetic radiation supplied can be directed as far as the distal end of the aspiration line.

The aspiration line can also have a line wall which passes on electromagnetic radiation coupled therein. The passing on of the electromagnetic radiation can be performed either by the material of the aspiration line itself, or by a light guide in the wall of the aspiration line. Such an embodiment is advantageous since thereby no fluid or lens particles present in the aspiration line can prevent the electromagnetic radiation from being passed on.

The control arrangement according to the invention has a control unit which can be used to control an absolute value of a parameter of the ophthalmic surgical system as a function of the absolute value of the received radiation. The parameter of the ophthalmic surgical system can be an ultrasonic energy supplied to a phaco handpiece by a power supply, a suction power of an aspiration pump, or a volume flow of a fluid for venting the aspiration line. The control unit can thereby cause the ultrasonic energy supplied to the phaco handpiece to be switched off in the case of the breakthrough of an occlusion such that the risk of damage to the capsular bag is reduced. Alternatively or in addition, in the case of the breakthrough of an occlusion the control arrangement can reduce, or switch off completely, a suction power of an aspiration pump such that the vacuum in the aspiration line is no longer maintained at the existing level. Alternatively or in addition, the control unit can supply a fluid to the aspiration line, thereby venting, so as to reduce the vacuum actively as a result.

The absolute value of the parameter of the ophthalmic surgical system can preferably be controlled as a function of the pressure in the aspiration line. For example, it is possible to provide that the control arrangement comes into use only once the vacuum in the aspiration line has reached a predetermined level. It is thereby possible to filter out artifacts and non-hazardous pressure fluctuations so as to eliminate hectic and unnecessary interventions of the control arrangement in the ophthalmic surgical system.

The ophthalmic surgical system for phacoemulsification of an eye lens has a control arrangement as described above and a system component unit which has a power supply for a phaco handpiece and/or an aspiration pump and/or a reflux container for receiving fluid for venting the aspiration line.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
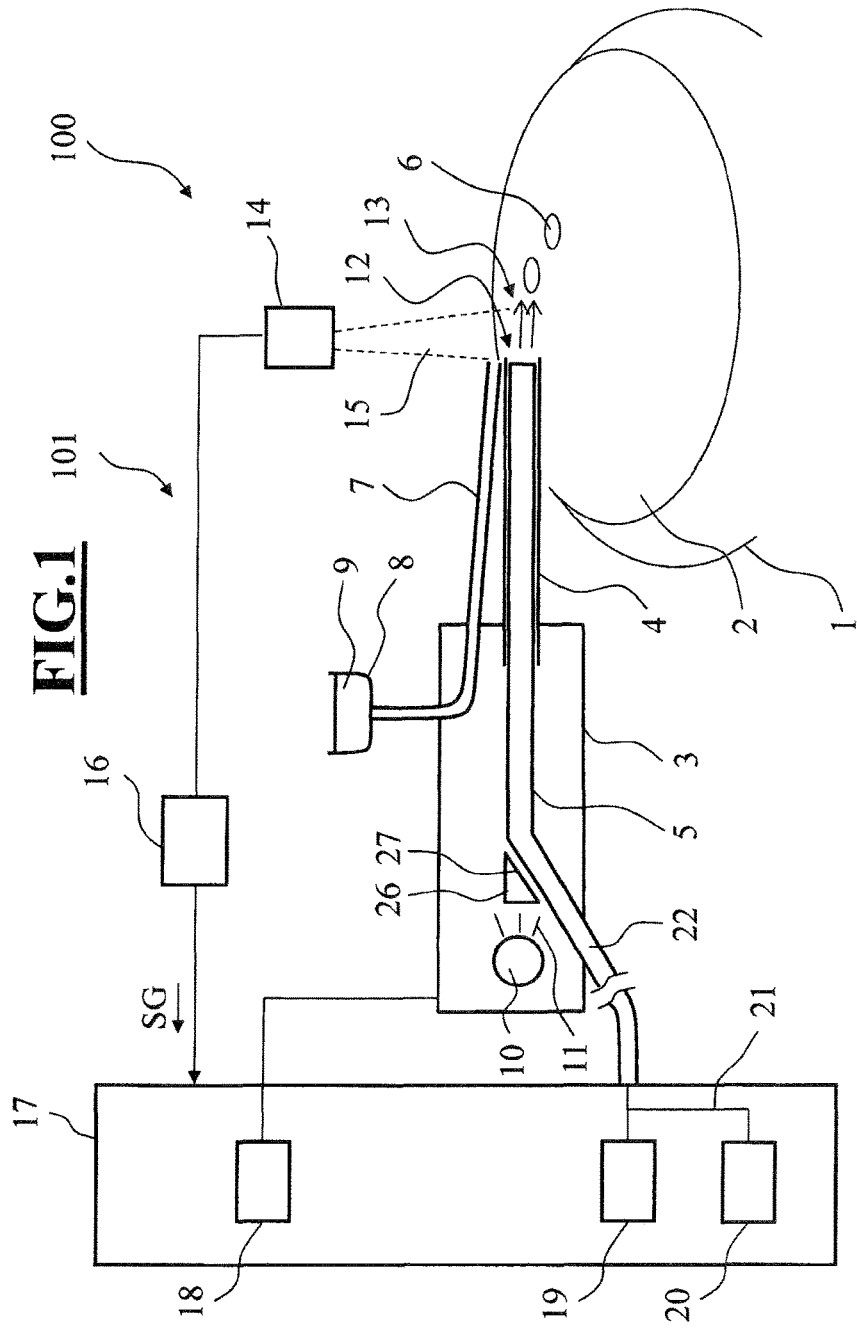
FIG. 1 is a schematic of an ophthalmic surgical system having a control arrangement in accordance with a first embodiment of the invention.

FIG. 1 illustrates an ophthalmic surgical system 100 having a control arrangement 101. An eye 1 has an eye lens 2 to be emulsified, a phaco handpiece 3 having been injected with a needle 4 into the lens 2. Inside the needle 4 there runs an aspiration line 5 which can be used to suction away shattered lens particles 6 and fluid. In addition, an irrigation fluid 9 is directed to the tip of the needle 4 from an irrigation fluid container 8 via an irrigation line 7. A transmitter 10 which can, for example, be arranged inside the phaco handpiece 3, emits electromagnetic radiation 11 to a coupling device 26. The coupling device 26 is suitable for receiving at least a portion of the emitted electromagnetic radiation 11, and thus to pass it on to a distal end 27 of the coupling device 26 arranged outside the aspiration line 5 such that the at least one portion of the electromagnetic radiation 11 can be coupled into the aspiration line 5. In the embodiment illustrated in FIG. 1, the electromagnetic radiation 11 is coupled, emanating from the distal end 27, into a straight section of the aspiration line 5. The radiation 11 can, however, also be coupled along an aspiration line 5 which is curved or provided with kinks, and be passed on from there, the transmitter 10 being arranged outside the handpiece. The electromagnetic radiation then exits at the distal end 12 of the aspiration line 5—see reference numeral 13—when the distal end 12 of the aspiration line 5 is not blocked by particles 6.

In this first embodiment, a receiver 14 is arranged such that it can detect the electromagnetic radiation exiting at the distal end 12. For this purpose, the receiver 14 has a receiving region 15 which includes at least a zone about the distal end 12 of the aspiration line 5. The radiation received by the receiver 14 is processed so as to determine whether or not there is an occlusion, and whether an occlusion is beginning or just breaking through. The information is fed to a control unit 16 which outputs a control variable SG to a system component unit 17 as a function of the information.

The system component unit 17 can have a power supply 18 which is, in turn, connected to the phaco handpiece 3. When it has been established by means of the receiver 14 that a breakthrough of an occlusion has taken place, the control unit 16 can drive the power supply 18 such that the needle 4 is no longer excited to ultrasonic vibrations. It follows that there is no further supply of power, and so the risk of damage to the lens capsule is less. The system component unit 17 can also have an aspiration pump 19 which is driven by the control unit 16, the aspiration pump 19 being connected to the aspiration line 5 which contains aspiration fluid 22. In the case of a breakthrough of an occlusion, the aspiration pump 19 is thereby stopped, or its direction of rotation is reversed. Furthermore, the system component unit 17 can also have a reflux container 20 which is driven by the control unit 16 such that a volume flow of a fluid is supplied for venting the aspiration line 5 by means of a reflux line 21.

The coupling device 26 can further have an optical light guide, for example an optical fiber, configured as a monomode or multimode fiber, or a lens.

If the aspiration line is transparent to electromagnetic radiation, the coupling of the electromagnetic radiation can be performed at any desired point of the aspiration line. If the aspiration line is not to be transparent to electromagnetic radiation, the aspiration line can be provided with a localized zone transparent to electromagnetic radiation.

Figure 2:
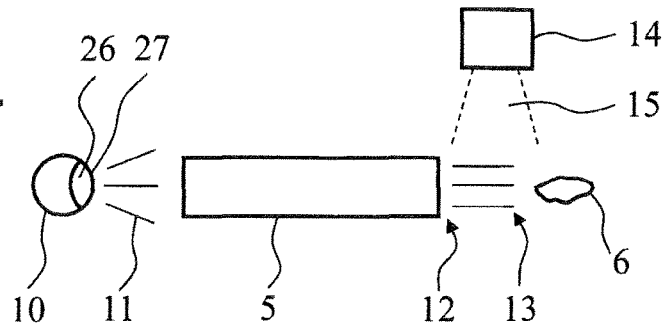
FIG. 2 is a schematic of an aspiration line and of a receiver when there is no occlusion of the aspiration line.

FIG. 2 is a greatly simplified schematic of the situation wherein an electromagnetic radiation exits the aspiration line 5 at the distal end 12, the distal end 12 of the aspiration line 5 not being blocked by a particle 6. The electromagnetic radiation 11 is emitted by a transmitter 10 via an optical lens as coupling device 26. In the embodiment shown in FIG. 2, the receiver 14 can receive the electromagnetic radiation exiting inside its receiving region 15—see reference numeral 13.

Figure 3:
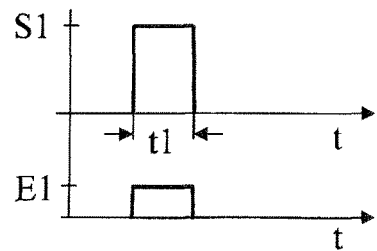
FIG. 3 is a schematic of signal profiles of a transmitter and of a receiver for an arrangement according to FIG. 2.

Illustrated in FIG. 3 are signal profiles which are to be expected in the situation in FIG. 2. During a time t1, the transmitter 10 emits an electromagnetic radiation 11 with the beam intensity S1. Virtually without time delay, the receiver 14 receives an electromagnetic radiation, exiting at the distal end 12, with a beam intensity E1 which is lower than the emitted signal strength S1. The signal strength E1 is lower than the signal strength S1 since the electromagnetic radiation 11 emitted by the transmitter 10 loses intensity on the way through the aspiration line 5.

Figure 4:
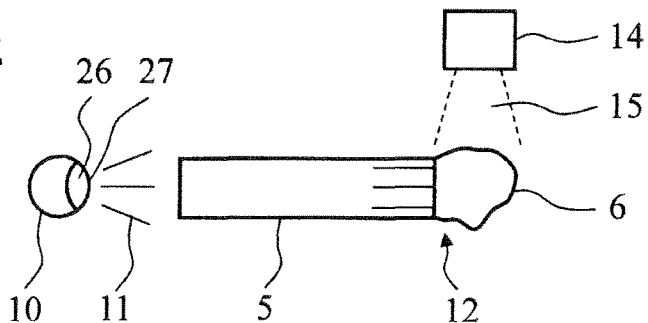
FIG. 4 is a schematic of an aspiration line and of a receiver in the case of an occlusion.

FIG. 4 shows a situation analogous to FIG. 2, but in the state when the aspiration line 5 is blocked at the distal end 12 with a lens particle 6. In this case, no electromagnetic radiation exits the aspiration line 5, and so the receiver 14 cannot receive electromagnetic radiation inside its receiving region 15.

Figure 5:
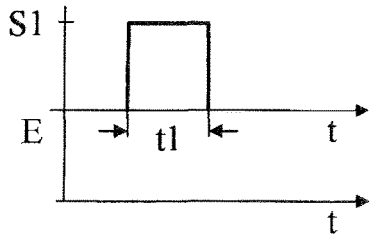
FIG. 5 is a schematic of signal profiles of a transmitter and of a receiver for the situation illustrated in FIG. 4.

FIG. 5 shows signal profiles for the transmitter 10 and the receiver 14 for the situation shown in FIG. 4. While the transmitter 10 is outputting an electromagnetic radiation 11 with a beam intensity S1, the receiver is unable to receive any electromagnetic radiation.

Figure 6:
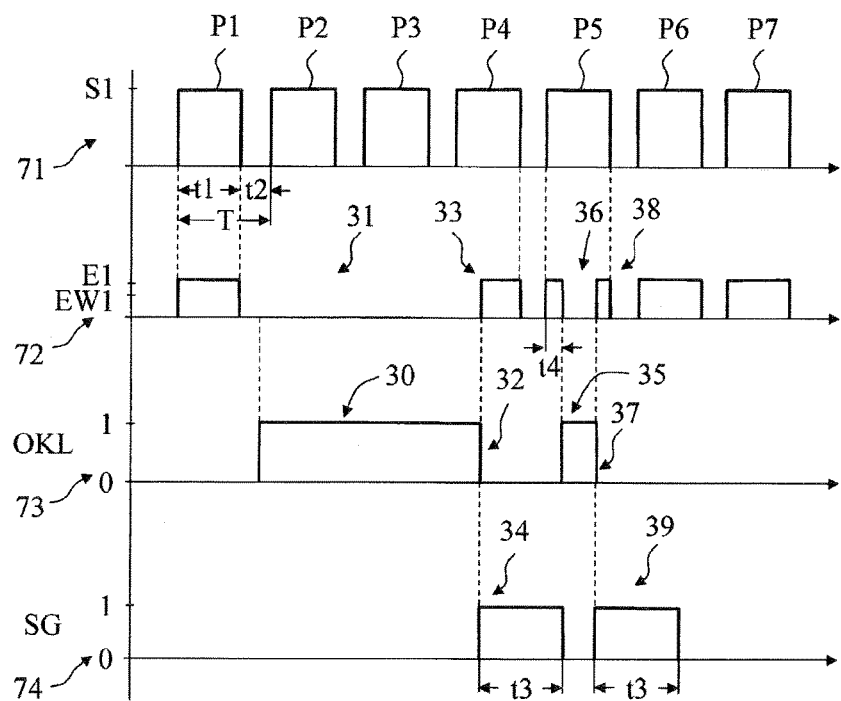
FIG. 6 is a schematic of the signal profiles of a transmitter and of a receiver as a function of different occlusion states.

FIG. 6 shows a plurality of graphs as a function of time. Graph 71 shows signal profiles for a transmitter 10, graph 72 shows signal profiles for a receiver 14, graph 73 shows signal profiles of existing or non-existing occlusion states of the aspiration line, and graph 74 shows profiles of a controlled variable SG. It is assumed that during a term t1 the transmitter emits an electromagnetic radiation with a beam intensity S1. During the term t2 following thereupon, the transmitter does not output any electromagnetic radiation, the pattern being repeated continuously with the terms t1 and t2. The transmitter therefore outputs a pulsed radiation with a period T. Thus, radiating is performed during pulse phases, denoted in FIG. 6 by P1, P2, P3, P4, P5, P6, P7, which are interrupted in each case by pulse pauses. During the first pulse phase P1 with the term t1, the receiver receives an electromagnetic radiation with the signal strength E1. During the subsequent term t2, in which the transmitter does not output electromagnetic radiation, it is assumed that the distal end of the aspiration line is blocked by a lens particle such that an occlusion occurs—see reference numeral 30 in graph 73. During the second pulse phase P2 of the transmitter, the receiver can therefore not receive any electromagnetic radiation—see reference symbol 31 in graph 72. It is assumed that the situation still exists during the third pulse phase P3. However, during the fourth pulse phase P4 there is an occlusion breakthrough—see reference numeral 32 in graph 73—so that it is possible immediately thereafter for the receiver again to receive an electromagnetic radiation with a signal strength above a predetermined threshold EW1—see reference symbol 33 in graph 72. The rise in signal strength to the level E1 is a reliable indicator that an occlusion breakthrough has taken place. In the case of the control arrangement according to the invention, the control unit outputs a controlled variable SG to a system component unit—see reference symbol 34 in graph 74—so that an absolute value of a parameter of the ophthalmic surgical system can be controlled. It is assumed that the controlled variable SG is present during a predetermined term t3.

At the beginning of the subsequent pulse phase P5, there is still no renewed occlusion. During the pulse phase P5, it is assumed that such an occlusion does however recur—see reference numeral 35 in graph 73. This is detected from the fact that the receiver can receive a signal with a reception strength E1 only briefly during a term t4. No signal can be detected by the receiver over the duration of the occlusion 35—see reference symbol 36 in graph 72. When the occlusion then breaks through during the pulse phase P5—see reference symbol 37 in graph 73—the receiver once again detects a signal with the signal strength E1—see reference symbol 38 in graph 72. The rise in signal strength of the receiver is a reliable indicator that an occlusion breakthrough has taken place so that the control unit outputs anew a controlled variable SG—see reference symbol 39 in graph 74—to the system component unit, whereupon it is possible to control an absolute value of a parameter of the ophthalmic surgical system. It is assumed that the controlled variable SG is present during a term t3. It may be assumed that no occlusion occurs in the pulse phases P6 and P7 following thereupon, so that the receiver can receive respective signal strengths at the level E1 during the entire continuous duration of transmission.

Figure 7:
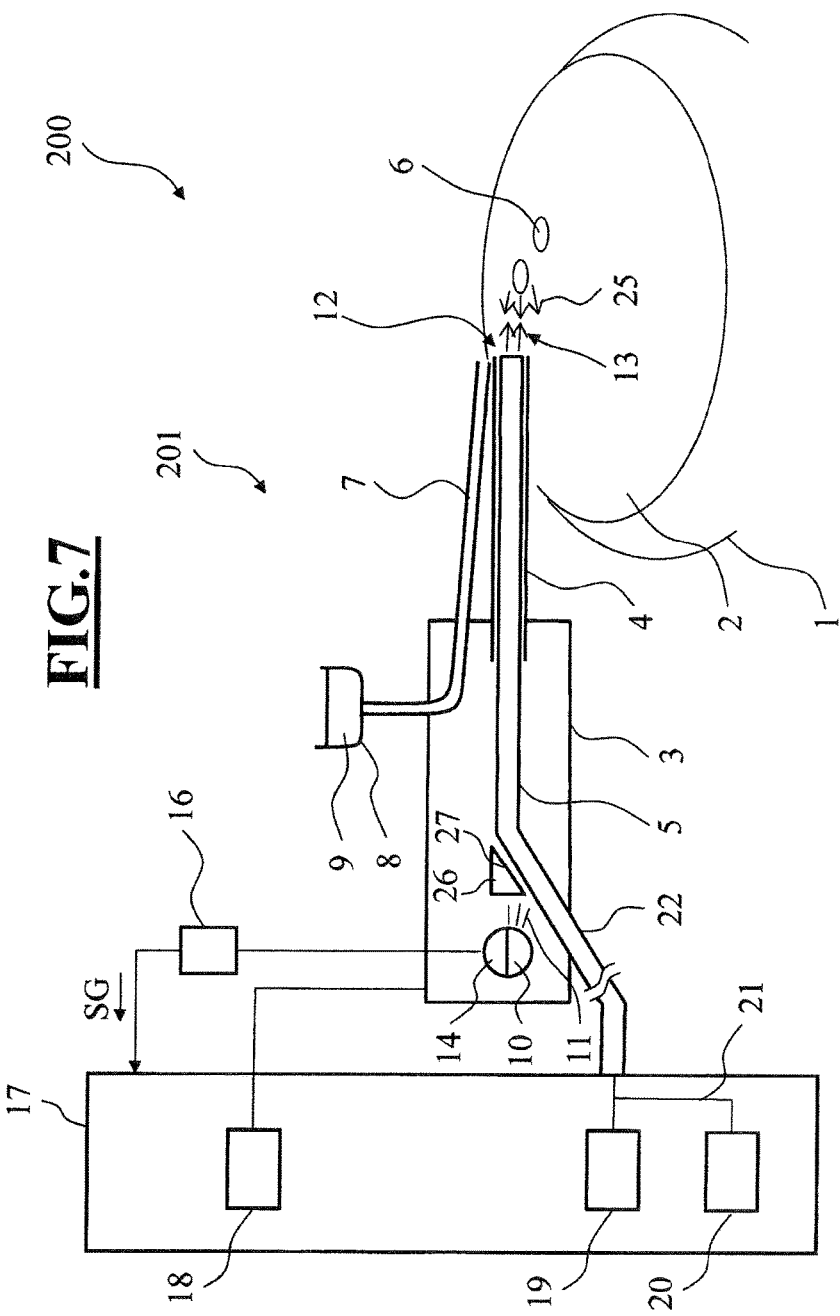
FIG. 7 is a schematic of an ophthalmic surgical system having a control arrangement in accordance with a second embodiment of the invention.

FIG. 7 illustrates an ophthalmic surgical system 200 having a control arrangement 201 in accordance with a second embodiment of the invention. The second embodiment differs from the first embodiment illustrated in FIG. 1 in that the receiver 14 no longer detects the electromagnetic radiation exiting at the distal end 12—see reference symbol 13, but instead detects a radiation 25 reflected by lens particles 6.

An electromagnetic radiation 11 is coupled into an aspiration line 5 by the transmitter 10 by means of a coupling device 26. When there is no occlusion—see FIG. 7—a portion of the electromagnetic radiation exiting at the distal end of the aspiration line 5—see reference symbol 13—can be reflected by a lens particle 6 as reflected radiation 25.

In the embodiment illustrated in FIG. 7, a single coupling element 26 is used in order to couple electromagnetic radiation 11 into the aspiration line and decouple reflected radiation 25 from the aspiration line 5 to the receiver 14. In the third embodiment, illustrated in FIG. 8, of a control arrangement 301 of an ophthalmic surgical system 300, a receiver 14, which can be arranged near the transmitter 10, receives at least a portion of the radiation 25 reflected by the lens particles 6 by means of a second coupling device 260 separated from the coupling device 26.

Figure 16:
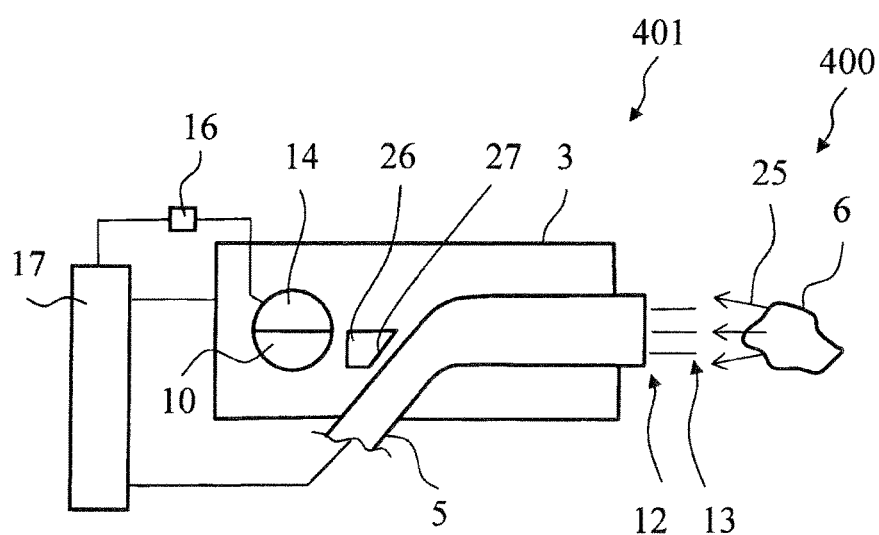

FIG. 16 is a schematic of a fourth embodiment of a control arrangement 401, according to the invention, of an ophthalmic surgical system 400. Here, the coupling device 26 can be configured such that only the electromagnetic radiation emitted by the transmitter 10 is passed on by means of the coupling device 26 and coupled into the aspiration line 5 via the distal end 27. The radiation 25 reflected by the lens particles 6 penetrates into the aspiration line 5 and is detected directly by the receiver 14 without a coupling device being arranged upstream thereof. This is advantageous when all that is still incident at the receiver is a reflected radiation 25 with a very low beam intensity, since as a result no further component can continue to weaken the beam intensity of the incident radiation 25.

Figure 8:
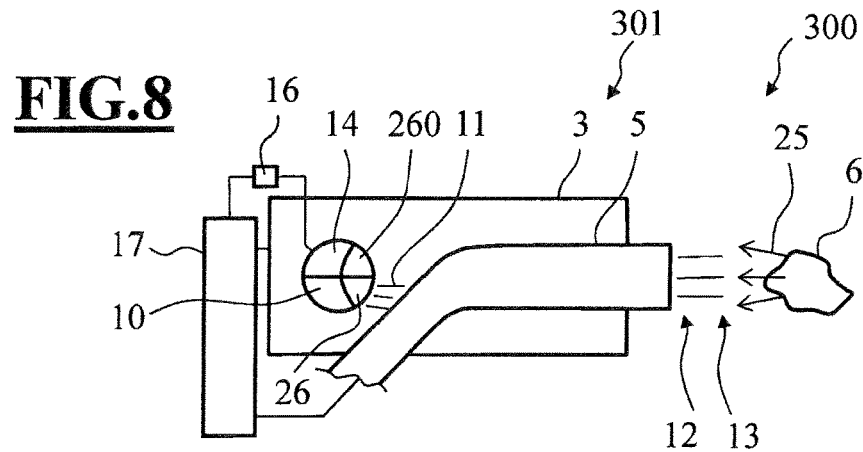
FIG. 8 is a schematic of an ophthalmic surgical system having a control arrangement in accordance with a third embodiment of the invention when there is no occlusion.
Figure 9:
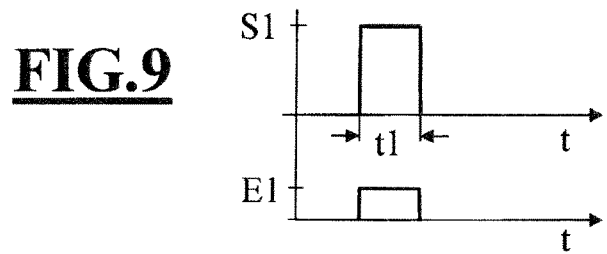
FIG. 9 is a schematic of signal profiles of transmitter and receiver for an embodiment in accordance with FIG. 8.

Associated signal profiles for the situation in accordance with FIG. 8 are illustrated schematically in FIG. 9. A transmitter 10 emits an electromagnetic radiation with a signal strength S1 during a time t1, and a receiver 14 receives an electromagnetic radiation with a signal strength E1 which is less than S1.

Figure 10:
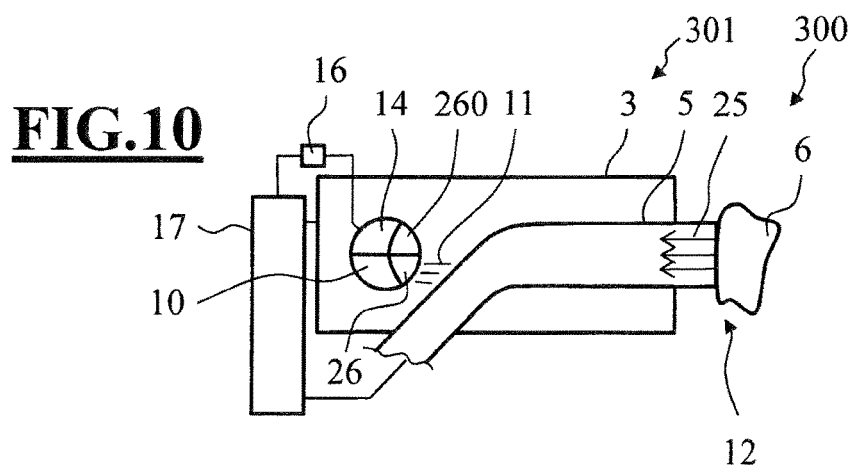
FIG. 10 is a schematic of a system in accordance with FIG. 8 when no occlusion is present.

FIG. 10 shows the situation for an occlusion of the aspiration line in the case of the third embodiment of the invention. In this case, all electromagnetic radiation 11 present in the aspiration line 5 is reflected by the lens particle 6 as reflected radiation 25 such that no electromagnetic radiation exits at the distal end 12 of the aspiration line.

Figure 11:
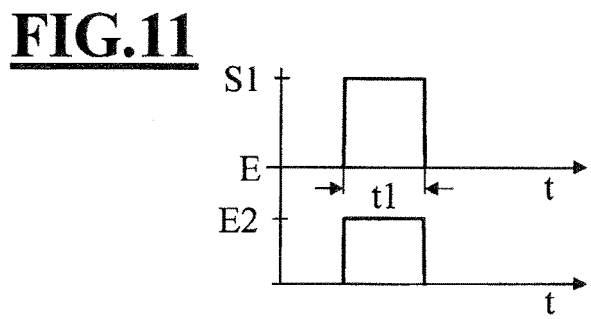
FIG. 11 is a schematic of signal profiles of transmitter and receiver for the situation in accordance with FIG. 10.

FIG. 11 shows the signal profiles associated with the situation illustrated in FIG. 10. When the transmitter emits during a time t1 an electromagnetic radiation with the signal strength S1, an electromagnetic radiation with a signal strength E2 can be received in the event of complete reflection at the lens particle 6. It can be assumed that the signal strength E2 is greater than E1 in the event of complete reflection.

Figure 12:
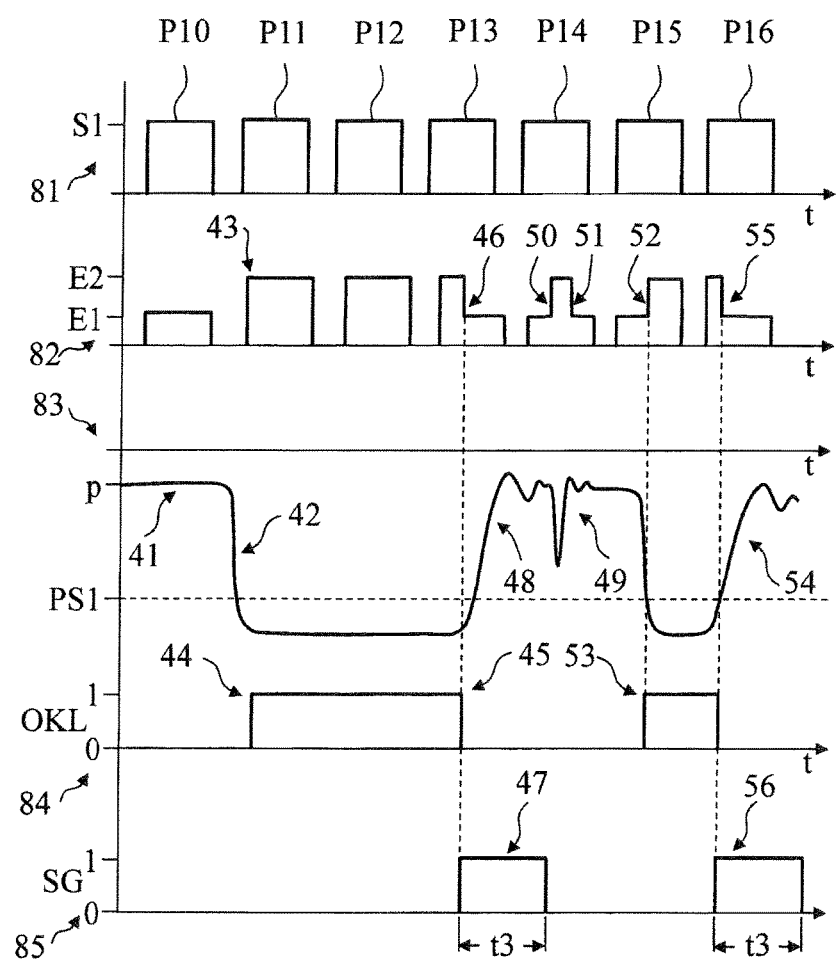
FIG. 12 is a schematic of signal profiles of transmitter and receiver as a function of different occlusion states, taking account of the pressure profile in an aspiration line.

FIG. 12 shows, for a control arrangement in accordance with the second embodiment, a plurality of graphs as a function of time. Graph 81 shows signal profiles for a transmitter 10, graph 82 shows signal profiles for a receiver 14, graph 83 shows a signal profile of a pressure in the aspiration line, graph 84 shows signal profiles for existing or nonexisting occlusion states of the aspiration line, and graph 85 shows profiles of a controlled variable SG. During a first pulse phase P10, a transmitter emits an electromagnetic radiation with a signal strength S1. When there is no occlusion, the receiver receives an electromagnetic radiation with a relatively low signal strength E1 in the case of a control arrangement in accordance with the second embodiment of the invention. During this time, there is only a relatively low vacuum in the aspiration line—see reference symbol 41 in graph 83. The vacuum in the aspiration line is raised if it is assumed that the aspiration line is blocked thereupon—see reference symbol 42 in graph 83. If a predetermined pressure threshold PS1 is exceeded, a check is made as to whether there is a change in the signal strength from E1 to a higher signal strength E2 in the pulse phase P11 following therefrom. This is the case in accordance with reference symbol 43 in graph 82, and so it is detected that the beginning of an occlusion of the aspiration line is present—see reference symbol 44 in graph 84. It is assumed that the occlusion is still present even in the pulse phase P12 following therefrom and during a portion of the pulse phase P13 following therefrom. If it is further assumed that the occlusion breaks through during the pulse phase P13—see reference symbol 45 in graph 84—this can be detected by the control arrangement according to the invention in that the signal strength at the receiver drops from the absolute value E2 to E1—see reference symbol 46 in graph 82. The change in the signal strength has the effect that the control unit 16 outputs a controlled variable SG to a system component unit 17—see reference symbol 47 in graph 85—the controlled variable being applied, for example, during a time t3. The pressure profile in the aspiration line drops substantially after the occlusion breakthrough—see reference symbol 48 in graph 83. If it is further assumed that, for example, short term pressure fluctuations occur thereupon during the subsequent pulse phase P14—see reference symbol 49 in graph 83—which lie, however, below the predetermined pressure threshold PS1, then despite a change in the signal strength from E1 to E2—see reference symbol 50 in graph 82—or from E2 to E1—see reference symbol 51 in graph 82—the fluctuation can still be interpreted as an artifact such that the control unit 16 still does not output a controlled variable SG. However, when the pressure profile exceeds the pressure threshold PS1, for example because an occlusion recurs, during a pulse phase P15 the signal strength of the receiver rises again from E1 to E2—see reference symbol 52 in graph 82—so that the beginning of an occlusion is detected—see reference symbol 53 in graph 84. When the occlusion breaks through during the pulse phase P16 following thereupon, so that the pressure in the aspiration line decreases again—see reference symbol 54 in graph 83—the signal strength of the receiver drops from E2 to E1 again—see reference symbol 55 in graph 82—whereupon the control unit 16 outputs a controlled variable SG to a system component unit 17—see reference symbol 56 in graph 85. The controlled variable SG can be applied again during a term t3.

Figure 13:
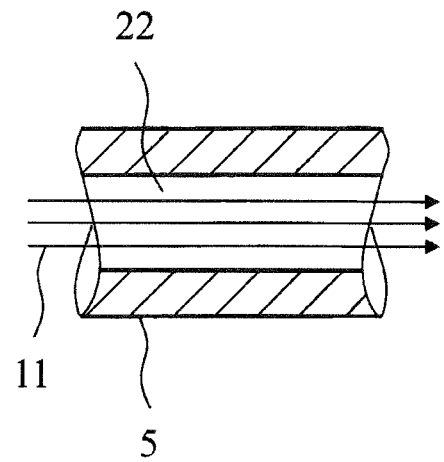
FIG. 13 shows a cross-sectional view of an aspiration line which passes on electromagnetic radiation by means of fluid.
Figure 14:
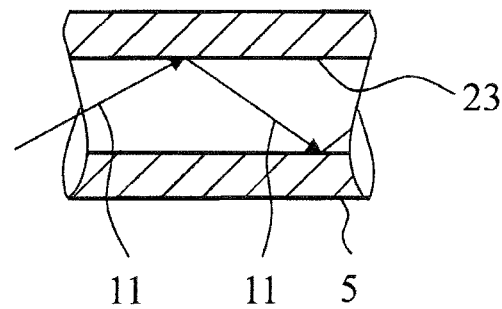
FIG. 14 shows a cross-sectional view of an aspiration line which has a line inner wall which reflects the electromagnetic radiation coupled into the aspiration line.
Figure 15:
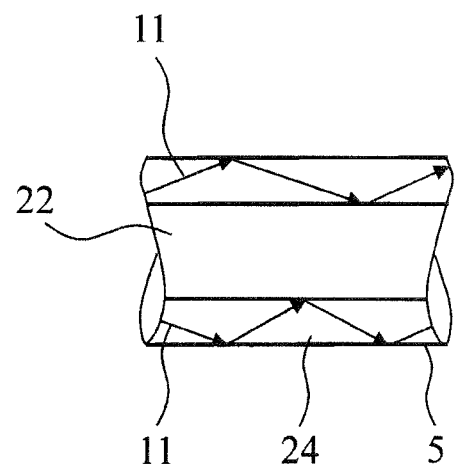
FIG. 15 shows a cross-sectional view of an aspiration line which has a line wall which passes on electromagnetic radiation coupled therein; and, FIG. 16 is a schematic of an ophthalmic surgical system having a control arrangement in accordance with a fourth embodiment of the invention.

FIGS. 13, 14 and 15 show different configurations of aspiration lines 5. FIG. 13 illustrates a cross-sectional view of an aspiration line 5 in the case of which the electromagnetic radiation 11 is directed through a fluid 22 present in the aspiration line 5. In addition or as an alternative thereto, the electromagnetic radiation 11 can also be reflected at an inner wall 23 of the aspiration line 5 such that the electromagnetic radiation is passed on by reflection—see FIG. 14. A further configuration of the aspiration line is shown in FIG. 15, in the case of which a line wall 24 enables a reflection of an electromagnetic radiation 11 coupled in inside the line wall 24.

It is understood that the foregoing description is that of the preferred embodiments of the invention and that various changes and modifications may be made thereto without departing from the spirit and scope of the invention as defined in the appended claims.

What is claimed is:

1. A control arrangement for an ophthalmic surgical system for phacoemulsifying an eye lens, the system including:
    an aspiration line for drawing off fluid and shattered lens particles of the eye lens;
    a phaco handpiece having a needle;
    said aspiration line running within said needle and being configured to impart ultrasonic energy to said phaco handpiece for shattering said eye lens via a longitudinal vibration of said needle; and,
    said control arrangement comprising:
    a transmitter configured to irradiate electromagnetic radiation;
    a coupling unit having a distal end and being configured to conduct at least one part of said irradiated electromagnetic radiation to said distal end;
    said distal end being disposed outside of said aspiration line so as to cause said at least one part of said electromagnetic radiation to be coupled into said aspiration line;
    a receiver configured to receive at least a part of said electromagnetic radiation;
    a control unit configured to control an absolute value of a parameter of said ophthalmic surgical system in dependence upon the amount of the received electromagnetic radiation; and,
    said electromagnetic radiation being a pulsed infrared radiation having an irradiance of a maximum of 0.1 W/cm$^2$ and said electromagnetic radiation having a wavelength greater than 750 nanometers.

2. The control arrangement of claim 1, wherein electromagnetic radiation coupled into said aspiration line emanates therefrom; and, said receiver is configured to receive the electromagnetic radiation emanating from said aspiration line.

3. The control arrangement of claim 1, wherein said receiver receives electromagnetic radiation reflected from a lens particle.

4. The control arrangement of claim 1, wherein said aspiration line has a line inner wall for reflecting the electromagnetic radiation coupled into said aspiration line.

5. The control arrangement of claim 1, wherein said aspiration line has a line wall for forward conducting electromagnetic radiation coupled thereinto.

6. The control arrangement of claim 1, wherein said control arrangement further comprises an energy supply for supplying ultrasonic energy to said phaco handpiece; an aspiration pump having a suction power and being operatively connected to said aspiration line; a reflux vessel for supplying a volume flow of a fluid for venting said aspiration line; and, said parameter of said ophthalmic surgical system being one of: said ultrasonic energy, said suction power or said volume flow.

7. The control arrangement of claim 6, wherein said absolute value of said parameter of said ophthalmic surgical system is controllable in dependence upon pressure in said aspiration line.

8. An ophthalmic surgical system for phacoemulsifying an eye lens, the system comprising:
    an aspiration line for drawing off fluid and shattered lens particles of the eye lens;
    a phaco handpiece having a needle;
    said aspiration line running within said needle and being configured to impart ultrasonic energy to said phaco handpiece for shattering said eye lens via a longitudinal vibration of said needle; and, a control arrangement including:

a transmitter configured to irradiate electromagnetic radiation;

a coupling unit having a distal end and being configured to conduct at least one part of said irradiated electromagnetic radiation to said distal end;

said distal end being disposed outside of said aspiration line so as to cause said at least one part of said electromagnetic radiation to be coupled into said aspiration line;

a receiver configured to receive at least a part of said electromagnetic radiation;

a control unit configured to control an absolute value of a parameter of said ophthalmic surgical system in dependence upon the amount of the received electromagnetic radiation;

said electromagnetic radiation being a pulsed infrared radiation having an irradiance of a maximum of 0.1 W/cm$^2$ and said electromagnetic radiation having a wavelength greater than 750 nanometers; and, a system component assembly including at least one of the following: an energy supply for supplying energy to said phaco handpiece, an aspiration pump operatively connected to said aspiration line and a reflux vessel for holding fluid for venting said aspiration line.

* * * * *